United States Patent
Ishii

(10) Patent No.: US 9,430,312 B2
(45) Date of Patent: Aug. 30, 2016

(54) AUTOMATED ANALYSIS SYSTEM

(71) Applicant: HITACHI HIGH-TECHNOLOGIES CORPORATION, Tokyo (JP)

(72) Inventor: Naomi Ishii, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 99 days.

(21) Appl. No.: 14/353,042

(22) PCT Filed: Oct. 23, 2012

(86) PCT No.: PCT/JP2012/077364
§ 371 (c)(1),
(2) Date: Apr. 21, 2014

(87) PCT Pub. No.: WO2013/065528
PCT Pub. Date: May 10, 2013

(65) Prior Publication Data
US 2014/0250339 A1   Sep. 4, 2014

(30) Foreign Application Priority Data

Oct. 31, 2011  (JP) ................ 2011-239753

(51) Int. Cl.
*G06F 11/34* (2006.01)
*G06F 11/07* (2006.01)
(Continued)

(52) U.S. Cl.
CPC ..... *G06F 11/0769* (2013.01); *G01N 35/00584* (2013.01); *G01N 35/00623* (2013.01);
(Continued)

(58) Field of Classification Search
CPC .... G06F 11/34; G06F 11/079; G06F 19/345; G06F 19/30
See application file for complete search history.

(56) References Cited

U.S. PATENT DOCUMENTS 5,695,718 A * 12/1997 Imai ................ G01N 35/00594
340/521
5,730,939 A * 3/1998 Kurumada ....... G01N 35/00663
422/64

(Continued)

FOREIGN PATENT DOCUMENTS

JP    07-260793 A    10/1995
JP    2003-195940 A    7/2003
JP    2010-176266 A    8/2010

OTHER PUBLICATIONS

Extended European Search Report received in corresponding European Application No. 12845689.4 dated Jul. 21, 2015.
(Continued)

*Primary Examiner* — Jigar Patel
(74) *Attorney, Agent, or Firm* — Mattingly & Malur, PC

(57) ABSTRACT

The system includes an analyzer that analyzes a sample, or a processing device that pre-processes the sample, and a management device that manages at least one of the analyzer and the processing device, wherein the management device includes: error detection means that detects errors in the analyzer or the processing device; storage means having stored therein an operator notification management table in which at least one operator is registered per kind of error; error notification means that notifies an error that the error detection means has detected to operators who are to individually handle the error, the means notifying on the basis of the operator notification management table and in accordance with the kind of error detected by the error detection means; and registration means that registers an operator, who has handled the error as a troubleshooter, among operators to whom the error was notified from the error notification means.

12 Claims, 9 Drawing Sheets

(51) Int. Cl.
*G01N 35/00* (2006.01)
*G01N 35/02* (2006.01)
*G01N 35/04* (2006.01)

(52) U.S. Cl.
CPC ....... *G01N35/025* (2013.01); *G01N 2035/009* (2013.01); *G01N 2035/0091* (2013.01); *G01N 2035/0413* (2013.01); *G01N 2035/0443* (2013.01); *G01N 2035/0444* (2013.01)

(56) References Cited

U.S. PATENT DOCUMENTS 5,746,977 A 5/1998 Imai et al.
5,891,178 A * 4/1999 Mann ................. A61N 1/37247
 607/27
2004/0081301 A1* 4/2004 Phillips .................. G06Q 30/04
 379/114.06
2006/0026474 A1* 2/2006 Honda ............... G03G 15/5075
 714/728
2006/0115135 A1* 6/2006 Dehmeshki ........... G06F 19/321
 382/128
2010/0274498 A1 10/2010 Naito

OTHER PUBLICATIONS

International Preliminary Report on Patentability received in International Application No. PCT/JP2012/077364 dated May 15, 2014.

* cited by examiner

FIG. 4

| NO. | MONITORING RESULT | NOTIFICATION OPERATOR ID |
|---|---|---|
| 01 | DATA ALARM FOR SYSTEMATIC ERROR 1 | 001, 002, 003 |
| 02 | DATA ALARM FOR ACCIDENTAL ERROR | 001, |
| 03 | DATA ALARM FOR SYSTEMATIC ERROR 2 | 001, 002, 003 |
| 04 | DATA ALARM FOR SYSTEMATIC ERROR 3 | 001, 002, 003 |
| 05 | DATA ALARM FOR SYSTEMATIC ERROR 4 | 001, 002, 003 |
| 06 | DATA ALARM FOR SYSTEMATIC ERROR 5 | 001, 002, 003 |
| : | : | : |
| 101 | REAGENT SHORTAGE ALARM | 001, |
| 102 | OUT-OF-REAGENT ALARM | 001, 002, 003 |
| : | : | : |
| 1401 | TUBE SHORTAGE ALARM | 401, |
| 1402 | OUT-OF-TUBE ALARM | 401, 402 |
| : | : | : |
| : | : | : |
| 10101 | RESET: REAGENT SHORTAGE ALARM | 001, |
| 10102 | RESET: OUT-OF-REAGENT ALARM | 001, 002, 003 |
| : | : | : |
| 11401 | RESET: TUBE SHORTAGE ALARM | 401, |
| 11402 | RESET: OUT-OF-TUBE ALARM | 401, 402 |

FIG. 5

| ALARM MANAGEMENT NUMBER | ALARM OCCURRENCE DATE/TIME | ALARM CODE | NOTIFIER CODE | TROUBLE-SHOOTER CODE | COMMENT | COMPLETION FLAG |
|---|---|---|---|---|---|---|
| 0610-00001 | 2010/06/10-09:30.20 | 08 | 001,002 | 001 | /NONE | 1 |
| 0610-00002 | 2010/06/10-09:50.20 | 02 | 001 | 002 | /NONE | 1 |
| 0610-00003 | 2010/06/10-10:30.15 | 09 | 001,002,003 | 001,002 | /NECESSARY TO CHANGE PROBES. | 0 |
| : | : | : | : | : | : | : |

FIG. 6

QUALITY CONTROL ALARM HAS OCCURRED.

DEVICE NUMBER : 001
QUALITY CONTROL SAMPLE : 101
TEST ITEM : 41-TP
TEST RESULT : 50.5
ERROR NUMBER : 08 QC1 DATA ALARM
TROUBLESHOOTER : UNSET

ARE YOU GOING TO TROUBLESHOOT THIS ERROR?

[ YES ]  [ NO ]
 502      503

AFTER-TROUBLESHOOTING RESULT REGISTRATION

QUALITY CONTROL ALARM
MANAGEMENT NUMBER : [ 0610-0001 ] —605
DEVICE NUMBER : 001
QUALITY CONTROL SAMPLE : 101
TEST ITEM: : 41-TP
TEST RESULT : 50.5
ERROR NUMBER : 08 QC1 DATA ALARM
TROUBLESHOOTER : 001 TAROH HITACHI
                  002 HANAKO HITACHI

COMMENT ON TROUBLESHOOTING RESULT:
[ NECESSARY TO CHANGE PROBES. ] —604

HAVE YOU FINISHED TROUBLESHOOTING ON THIS ERROR?

[ YES ]  [ NO ]
 602      603

| | | | 1600 | | | | |
|---|---|---|---|---|---|---|---|
| 1602 | 1601 | 1603 | | 1604 | 1605 | 1606 | 1611 |

1612 { | ALL | NOW TROUBLESHOOTING | ALARM IN CHARGE | COMPLETED | SUPPORT REQUEST |

ALARM LIST    11:23-12 / 11:20-12

1607 {
| PRE-PROCESSING DEVICE 001 WARNING 101 | 13:14-18 |
| SHORTAGE OF REAGENT    NO ACTION TAKEN YET. | |
| DEVICE 002 WARNING 101 | 11:20-18 |
| SHORTAGE OF REAGENT    NO ACTION TAKEN YET. | |
| DEVICE 003 WARNING 101 | 10:15-43 |
| REAGENT 222 ZERO LEVEL    IN CHARGE | 11:16-32 |
| DEVICE 002 WARNING 102 | 11:10-23 |
| CLEANING LIQUID A ZERO LEVEL   SUPPORT REQUESTED TO HANAKO HITACHI. | |
| DEVICE 001 WARNING 101 | 11:05-25 |
| REAGENT 393 SHORTAGE   ACTION BEING TAKEN BY TAROH HITACHI. | |
| DEVICE 031 WARNING 101 | 10:53-28 |
| REAGENT 338 SHORTAGE   ACTION BEING TAKEN BY TAROH HITACHI. | |
| DEVICE 001 WARNING 101 | 10:01-23 |
| REAGENT 910 SHORTAGE   ACTION COMPLETED. | 10:10-53 |

1613 { | ALARM | HELP? | SET |
           1608     1609    1610 though the responsible person designated as the person who should
AUTOMATED ANALYSIS SYSTEM

TECHNICAL FIELD

The present invention relates to an automated analysis system that analyzes biological samples of blood, urine, and the like.

BACKGROUND ART

For their advantages such as rapid analytical processing and high reproducibility of analytical results, automated analysis systems that analyze biological samples of blood, urine, and the like, are absolutely necessary for diagnosis of today. Automated analysis systems of this type come in a plurality of versions to suit different kinds of analysis. These versions are, for example, a colorimetric analyzer for conducting biochemical analyses, an immunoassay analyzer for with the use of antigen-antibody reactions to analyze the antigen or antibody contained in a sample, a coagulation analyzer for analyzing the ability of blood to clot, and a blood cell counter for determining the number of blood cell components contained in blood. Prior to the analysis of a sample with an automated analysis system, sample processing devices are also used that execute pre-processing such as centrifuging blood and/or dispensing the sample to create a plurality of child samples. At one hospital/clinic, biochemical test center, or the like, it is common that the above automated analysis systems and sample processing devices are each used in plurality.

If an error occurs in these automated analysis systems and/or sample processing devices, failure to undertake urgent countermeasures could lead to an interruption in a flow of the analysis or to a delay in a doctor's diagnosis. Accordingly, there is known a technique, as in Patent Document 1, intended to undertake urgent countermeasures by notifying the system/device error to a person responsible for the management of the system or device.

PRIOR ART LITERATURE

Patent Document

Patent Document 1: JP-1995-260793-A

SUMMARY OF THE INVENTION

Problems to be Solved by the Invention

The technique described in Patent Document 1 allows the occurrence of the error to be notified to the responsible person capable of taking an appropriate corrective action according to the kind of error. There exists a problem, however, that other persons cannot tell whether the appropriate action has been taken since the other persons will probably have no idea how the responsible person to whom the occurrence of the error was notified has later handled the error. In addition, a delay in the action is probable when the responsible person designated as the person who should handle the error is unable to act immediately for a reason such as temporarily having left his/her seat.

An object of the present invention is to provide an automated analysis system configured such that even if an error occurs in an analyzer, a processing device, or the like, operators will be able to share information on who has handled the error.

Means for Solving the Problems

In order to attain the above object, an aspect of the present invention includes a mechanism that automatically notifies to previously registered operators an error that has occurred. In the mechanism, information indicating a particular operator handles the error will also be shared among the other registered operators when one of the operators to whom the occurrence of the error has been notified shows his/her intention to handle the error.

Effect of the Invention

In accordance with the above aspect of the present invention, information on who has handled the error can be shared among a plurality of operators even if an error occurs in an analyzer, a processing device, or the like.

BRIEF DESCRIPTION OF THE DRAWING

FIG. 4 is a conceptual diagram showing an example of a notification destination management table in the automated analysis system according to the embodiment of the present invention.

FIG. 5 is a conceptual diagram showing an example of a notification result management table in the automated analysis system according to the embodiment of the present invention.

FIG. 6 is a diagram showing an example of a screen displayed on display means of an external terminal provided in the automated analysis system according to the embodiment of the present invention.

FIG. 7 is a diagram showing an example of a trouble-shooting result registration screen in the automated analysis system according to the embodiment of the present invention.

FIG. 16 is a diagram showing an example of an analyzer/processing device alarm list screen displayed at the external terminal provided in the automated analysis system according to the embodiment of the present invention.

MODE FOR CARRYING OUT THE INVENTION

Hereunder, an embodiment of the present invention will be described with the use of the accompanying drawings.

Figure 1:
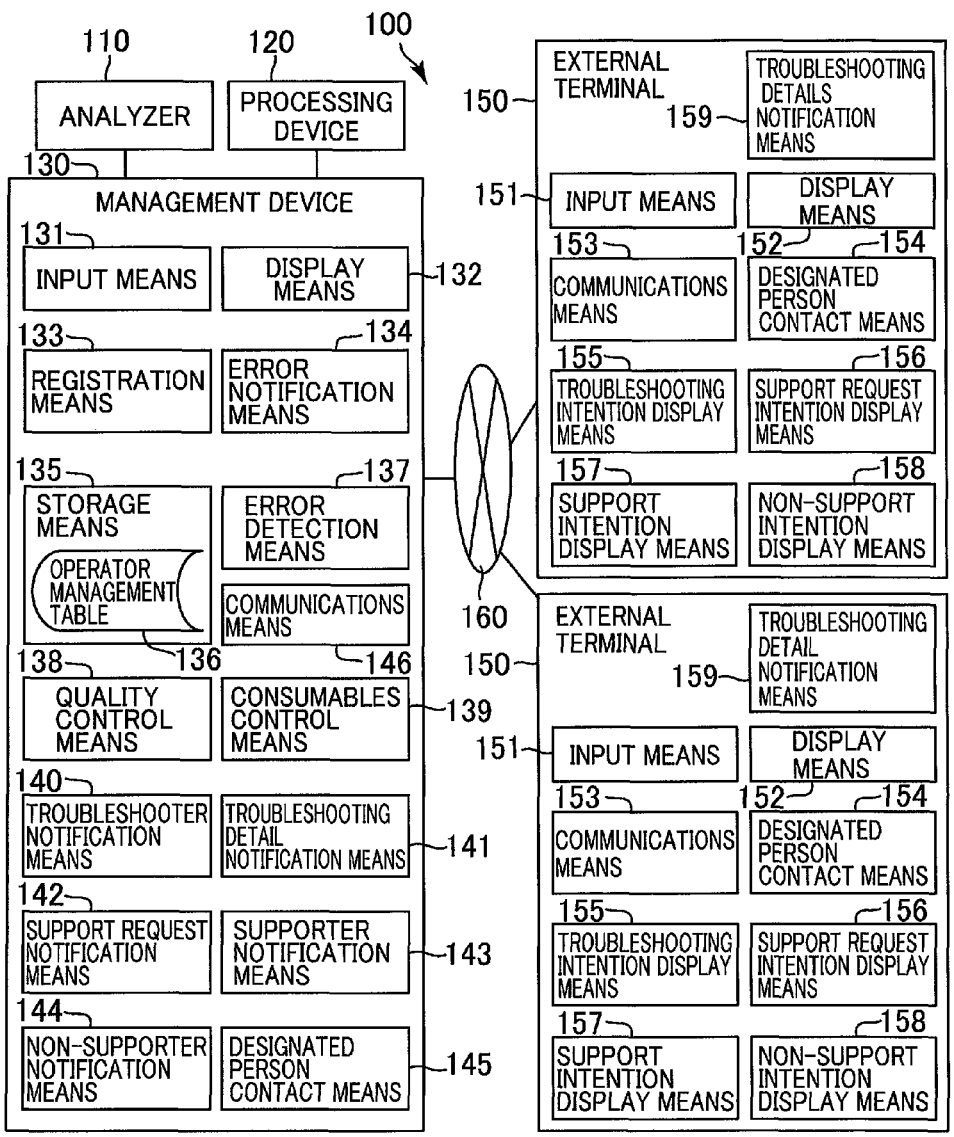
FIG. 1 is a block diagram showing a schematic configuration of an automated analysis system according to an embodiment of the present invention.

FIG. 1 is a block diagram showing a schematic configuration of an automated analysis system according to an embodiment of the present invention.

The automated analysis system shown in the figure includes an analyzer 110 that analyzes a sample, a processing device 120 that pre-processes the sample, a management device 130 that manages the analyzer 110 and the processing device 120, and a plurality of external terminals, each of which one operator is to use independently (although two terminals only are shown as an example in the figure, more terminals may exist). The analyzer 110 and the processing device 120 do not always need to be connected together to the management device 130. There could be a combination of the analyzer 110 and the management device 130, as well as the processing device 120 and the management device 130.

The management device 130 includes input means 131, display means 132, registration means 133, error notification means 134, storage means 135, error detection means 137, quality control means 138, consumables control means 139, troubleshooter notification means 140, troubleshooting detail notification means 141, support request notification means 142, supporter notification means 143, non-supporter notification means 144, designated person contact means 145, and communication means 146.

The input means 131 includes, for example, a keyboard, a mouse, and other input means that uses a touch screen of the display means 132 and that may be used as the display means 132 as well. The display means 132 is a monitor that displays input information and other result information.

The registration means 133 registers notification destination operator information that has been entered through the input means 131, in an operator notification management table 136 stored into the storage means 135. The registration means 133 also records, in the storage means 135, identification information on an operator and details on troubleshooting by the operator (troubleshooter), who has taken a corrective action to an error, among those have been notified of the error from the error notification means 134. The operator notification management table 136, in which at least one operator is registered per kind of error as a candidate who is available as a troubleshooter to cope with the error, includes followings: a notification destination management table 1361 (see FIG. 4) for managing notification destinations; and a notification result management table 1362 (see FIG. 5) for managing, in accordance with a notified result, a state of the action taken by the troubleshooter. The communication means 146 receives the notification from the external terminal 150 and delivers the notification to a corresponding functional block.

The error detection means 137 detects errors that have occurred in the analyzer 110, the processing device 120, and the management device 130. More specifically, the error detection means 137 receives error signals from the analyzer 110, the processing device 120, and the management device 130 to thereby detect, for example, occurrence and detail of a quality control error, a lack of a residual quantity of a reagent, or malfunction in the analyzer 110, or a lack of a residual quantity of consumables, malfunction, or other errors in the processing device 120.

The error notification means 134 notifies the occurrence and details of an error which has been detected by the error detection means 137, to an appropriate operator via a network 160. In this case, the error notification means 134 conducts the notification to only the terminal, of all the external terminals 150, assigned to an operator who corresponds to the kind of error registered in the operator notification management table 136. The network 160 can be either of a wired local area network, a wireless local area network, a hand-held telephone line network, and a combination of these networks.

The quality control means 138 is a functional block that executes quality control examination of the analyzer 110, and the consumables control means 139 is a functional block that controls the quantities of reagent and other consumables left in the analyzer 110. An analytical accuracy error recognized as a result of the quality control examination of the analyzer 110 by way of the quality control means 138, or the lack of the residual quantity of reagent recognized under the control of the consumables control means 139 is an example of an error notified to the external terminal 150 of the responsible operator via the error notification means 134. Further details of the control by the quality control means 138 and the consumables control means 139 will be shown and described with examples later herein.

The troubleshooter notification means 140 is a functional block that transmits troubleshooter identification information as a notification to the error-notified operators other than the troubleshooter. Through the notification from the troubleshooter notification means 140, who took the action is informed to the error-notified operators other than the troubleshooter. When a notification of the corresponding operator's intention from a troubleshooting intention display means 155 (described later) of the external terminal 150 is input via the communication means 146, the above notification by way of the troubleshooter notification means 140 will be transmitted to the external terminals 150 of the operators to whom the notification is to be given.

The troubleshooting detail notification means 141 is a functional block that notifies details of troubleshooting to the error-notified operators other than the troubleshooter. Through the notification from the troubleshooting detail notification means 141, the details of the action which was taken to the error by the operator (troubleshooter) are informed to the error-notified operators other than the troubleshooter. The notification from the troubleshooting detail notification means 141 is a statement, comment, or other information relating to the details of the action that have been entered into troubleshooting detail notification means 159 (described later) of the external terminal 150 by the troubleshooter.

The support request notification means 142 is a functional block that notifies a support request from the troubleshooter, to the error-notified operators other than the troubleshooter. Through the notification from the support request notification means 142, the troubleshooter's intention to make the support request is informed to the error-notified operators other than the troubleshooter to whom the error has been notified. When support request intention display means 156 (described later) of the external terminal 150 is operated by the troubleshooter, the notification from the support request notification means 142 will be delivered in accordance with the information entered via the support request intention display means 156.

The supporter notification means 143 is a functional block that notifies, to the other error-notified operators, the identification information relating to operators who have accepted the support request. When support intention display means 157 (described later) of the external terminal 150 is operated by operators who show their intentions to provide the support, the notification from the supporter notification means 143 will be delivered to each of these operators according to the information entered via the support intention display means 157.

The non-supporter notification means 144 is a functional block that notifies the identification information relating to operators who have showed their intentions not to be in a position to accept the support request from the troubleshooter for whatever reason, to the error-notified operators other than those who have showed their intentions to provide the support. When non-support intention display means 158 (described later) of the external terminal 150 is operated by the operators who show their intentions not to be in a position to provide the support, the notification from the non-supporter notification means 144 will be delivered in accordance with the information entered via the support intention display means 158. The notification will be delivered to each of the operators other than those who have showed not to be in a position to provide the support.

The designated person contact means 145 is a functional block which, for example, if a notification that requests communication with a specific operator is received from an external terminal 150, transmits the notification that has been received from the notifier to the designated operator. The designated person contact means 145 is also a functional block that relays direct communication between operators via the respective external terminals 150, in which case the designated person contact means 145 allows, for example, telephone calls or character data, image data, or audio data exchanges to be exchanged between operators. For example, if the troubleshooter seeks for support or advice from a specific operator, the designated person contact means 145 allows the troubleshooter to specify a particular operator with whom to communicate or exchange data. The designated person contact means 145 further allows the system to have a function that notifies, to other operators and an upper-level administrator, detail of a telephone call that have been recorded with the use of a recording function assigned to an external terminal 50, as well as an image or video that has been acquired with the use of a still image or full-motion video acquisition function.

The external terminal 150 includes input means 151, display means 152, communication means 153, designated person notification means 154, troubleshooting intention display means 155, support request intention display means 156, support intention display means 157, non-support intention display means 158, and troubleshooting detail notification means 159. While the external terminal 150 is desirably a hand-held terminal that the operator can easily carry with him or her, it can be either a notebook type or desktop type of a personal computer, the number of which can be one or more than one.

The input means 151 can be of a touchscreen type or can be a keyboard, for example. The display means 132 is a monitor that displays contents of a notification, entered information, and other information, and that can have a function of the input means 151 as well. The external terminal 150 uses the communication means 153 to receive error information and other information sent from the management device 130 via the network 160, and uses the display means 152 to notify the received information to operators, at which time a voice, a warning sound, or the like may also be output together with the information.

The troubleshooting intention display means 155 is operation output means that the operator to whom the error has been notified from the error notification means 134 of the management device 130 operates if the operator in question intends to troubleshoot. When the troubleshooting intention display means 155 is operated by the operator (or an operator ID is entered), the intention of this operator to troubleshoot is transmitted to the management device 130. Thus the identification information relating to the operator who has showed his/her intention to troubleshoot is transmitted through the troubleshooter notification means 140 to the terminals 150 of the other operators with whom the corresponding error has been associated.

The troubleshooting detail notification means 159 is means used for the troubleshooter to enter a comment or other information relating to the details of troubleshooting. The details of troubleshooting by the troubleshooter are entered into the troubleshooting detail notification means 159 and then transmitted to the management device 130. Thus the details of troubleshooting are transmitted through the troubleshooting detail notification means 141 to the terminals 150 of the other operators associated with the error.

The support request intention display means 156 is operation output means, by use of which the troubleshooter operates to call for the other operators to provide the support relating to the error if the troubleshooter needs the support from other operators. When the support request intention display means 156 is operated, the support request from the troubleshooter is transmitted to the management device 130, whereby the support request is then transmitted through the support request notification means 142 to the terminals 150 of the other operators associated with the error.

The support intention display means 157 is operation output means used for an operator to show his/her intention to accept the support request of the troubleshooter and provide the support. When the support intention display means 157 is operated, the intention of the operator to provide the support is transmitted to the management device 130. Thus the identification information relating to the operator who has showed his/her intention to provide the support is transmitted through the supporter notification means 143 to the terminals 150 of the other operators associated with the error.

The non-support intention display means 158 is operation output means used for an operator to show his/her intention not to be in a position to provide the support with the support request of the troubleshooter. When the non-support intention display means 158 is operated, the intention of the operator not to be in a position to provide the support is transmitted to the management device 130. Thus the identification information relating to this operator (non-supporter) is transmitted through the non-supporter notification means 144 to the terminals 150 of the other operators associated with the error.

The designated person notification means 154 is operation output means used for the troubleshooter, for example, to designate a specific operator to be notified that the troubleshooter wishes to ask for support. When the designated person notification means 154 is operated, the information identifying the troubleshooter-designated operator is transmitted to the management device 130. Thus the troubleshooter's intention to request the support is notified to the terminal 150 of the designated operator via the designated person contact means 145.

In the present embodiment, information on who is going to troubleshoot an error event such as a quality control error, reagent shortage error, and consumables shortage error can be shared among a plurality of operators. If it is confirmed that at least one troubleshooter is present, the other operators will be able to continue their ongoing jobs.

In the present embodiment, information on details of the troubleshooting action which has been taken to the error event by the troubleshooter can also be shared among the plurality of operators. The present embodiment further allows the operators to evaluate appropriateness of the troubleshooting action. If the troubleshooting action lacks appropriateness, the sharing of the above information also allows those operators to give appropriate instructions or advice to the troubleshooter, which contributes to enhancing the rate of operation of the automated analyzer, the sample processing device, and the like.

In addition, the troubleshooter will be able to troubleshoot the error event more flexibly and more efficiently by way of requesting support from the other operators. Even if for some reason the operator who has been registered as the troubleshooter is not able to deal with the error, he or she can notify that situation to other operators. This means that it is possible to suppress a delay in troubleshooting due to, for example, a case where the operator and others may only take a wait-and-see position through unnecessarily shying away from undertaking the job.

First Example

An example of with the use of the automated analysis system according to the present embodiment is described below. The description relates to handling a quality control error in the analyzer 110.

Figure 2:
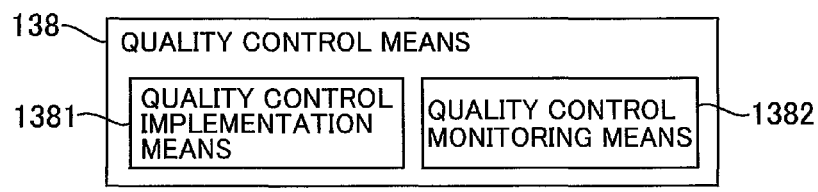
FIG. 2 is a functional block diagram of quality control means of a management device provided in the automated analysis system according to the embodiment of the present invention.

FIG. 2 is a functional block diagram of the quality control means 138 of the management device 130.

As shown in FIG. 2, the quality control means 138 includes quality control implementation means 1381 and quality control monitoring means 1382.

The quality control implementation means 1381 commands the analyzer 110 to conduct quality control tests, and the quality control monitoring means 1382 determines whether the quality control tests by the analyzer 110 indicate an error. More specifically, the analyzer 110 conducts the quality control tests with quality control samples and a reagent in accordance with the command of the quality control implementation means 1381, and sends the test results to the quality control means 138. The quality control means 138 uses the quality control monitoring means 1382 to execute statistical processing of the test results received from the analyzer 110 and thus to implement quality control of the analyzer 110.

Figure 3:
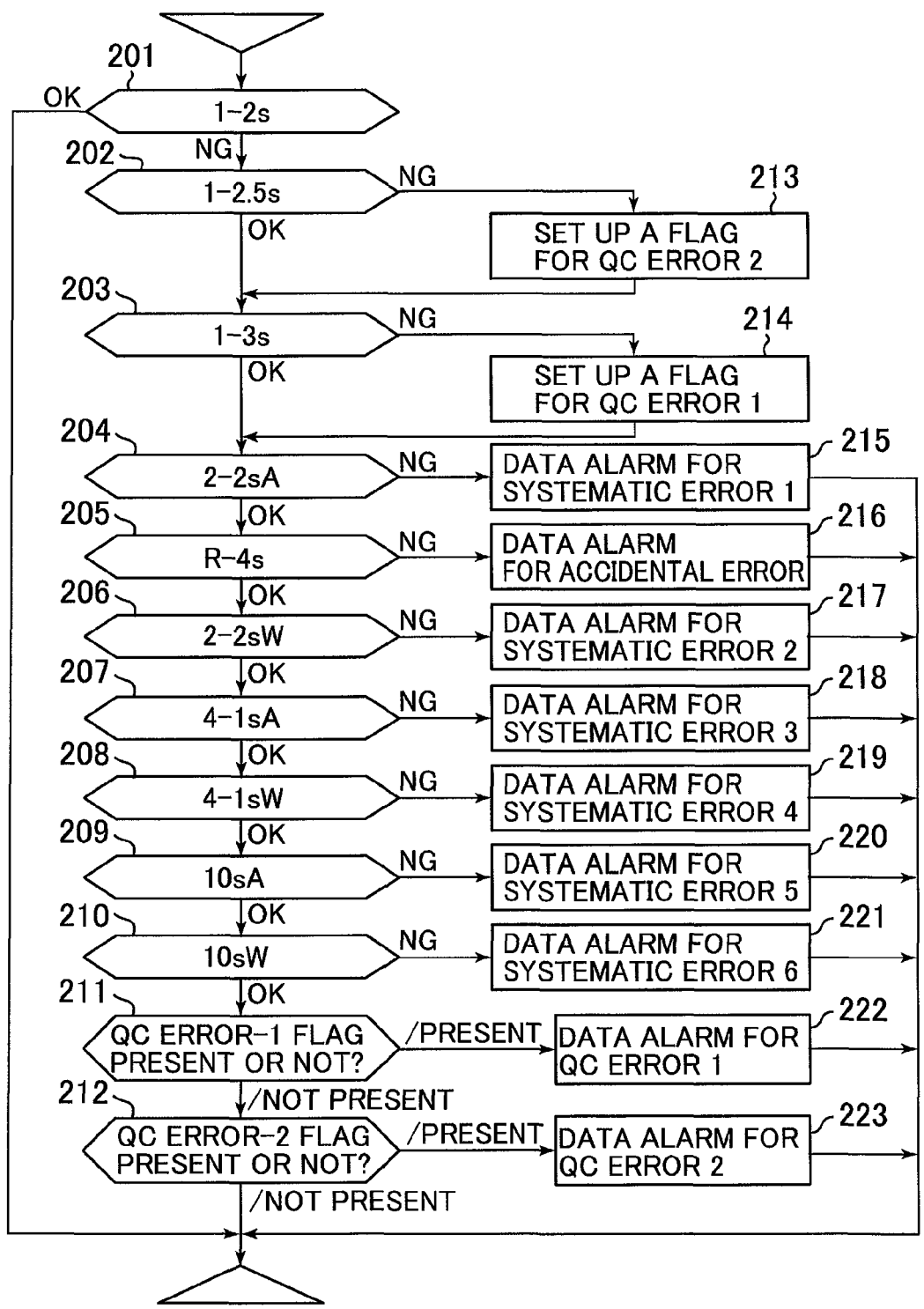
FIG. 3 is a flowchart showing an example of a determination sequence executed by quality control monitoring means provided in the automated analysis system according to the embodiment of the present invention.

FIG. 3 is a flowchart showing an example of a determination sequence executed by the quality control monitoring means 1382.

The example shown here relates to providing two kinds of quality control samples that generate different results from reactions with the same reagent, and determining whether a test error is ascribable to either a substance or an analyzer. The quality control monitoring means 1382 executes the following steps in order: step 201 to determine whether either of the two kinds of quality control sample test results has overstepped +/−2.0 SD of a control data criterion (SD: standard deviation); step 202 to determine whether either of the two kinds of test results falls within +/−2.5 SD of the control data criterion; step 203 to determine whether either of the two kinds of test results falls within +/−3.0 SD of the control data criterion; step 204 to determine whether either of the two kinds of quality control sample test results is within +2.5 SD or −2.5 SD of the control data criterion; step 205 to determine whether one of the two kinds of test results is greater than +2.0 SD of the control data criterion and the other is smaller than −2.0 SD; step 206 to determine whether either of the two kinds of test results has overstepped +2.0 SD or −2.0 SD of the control data criterion twice in succession; step 207 to determine whether both of the two kinds of test results have overstepped +2.0 SD or −2.0 SD of the control data criterion twice in succession; step 208 to determine whether either of the two kinds of test results has overstepped +1.0 SD or −1.0 SD of the control data criterion four times in succession; step 209 to determine whether both of the two kinds of test results lie on the plus side or minus side of the control data criterion five times in succession; and step 210 to determine whether either of the two kinds of test results lies on the plus side or minus side of the control data criterion 10 times in succession.

When both of the two kinds of test results fall within +/−2.0 SD of the control data criterion and the determination in step 201 is not satisfied, an error is not occurring particularly and this status is notified to the management device 130. If the determination in step 202 is not satisfied, a flag for QC error 2 is set up in step 213 and the sequence is shifted to step 203. If the determination in step 203 is not satisfied, a flag for QC error 1 is set up in step 214 and the sequence is shifted to step 204.

In addition, if both of the two kinds of sample test results have overstepped +/−2.0 SD and the determination in step 204 is not satisfied, the sequence is shifted from step 204 to step 215 in which a data alarm for systematic error 1 is then set and the alarm (including QC error 1 or 2 if either is set) is transmitted to the management device 130. If the determination in step 205 is not satisfied, the sequence is shifted from step 205 to step 216, in which step, a data alarm for an accidental error is then set and the alarm (including QC error 1 or 2 if either is set) is transmitted to the management device 130. If the determination in step 206 is not satisfied, the sequence is shifted from step 206 to step 217, in which step, a data alarm for systematic error 2 is then set and the alarm (including QC error 1 or 2 if either is set) is transmitted to the management device 130. If the determination in step 207 is not satisfied, the sequence is shifted from step 207 to step 218, in which step, a data alarm for systematic error 3 is then set and the alarm (including QC error 1 or 2 if either is set) is transmitted to the management device 130. If the determination in step 208 is not satisfied, the sequence is shifted from step 208 to step 219, in which step, a data alarm for systematic error 4 is then set and the alarm (including QC error 1 or 2 if either is set) is transmitted to the management device 130. If the determination in step 209 is not satisfied, the sequence is shifted from step 209 to step 220, in which step, a data alarm for systematic error 5 is then set and the alarm (including QC error 1 or 2 if either is set) is transmitted to the management device 130. If the determination in step 210 is not satisfied, the sequence is shifted from step 210 to step 221, in which step, a data alarm for systematic error 6 is then set and the alarm (including QC error 1 or 2 if either is set) is transmitted to the management device 130.

Conversely if the determinations in steps 204-210 are all satisfied, the sequence is shifted to step 211 and a determination is conducted whether the flag for QC error 1 is set up. If the flag for QC error 1 is set up, the sequence is shifted to step 222, in which step, a data alarm for QC error 1 is then set and the alarm is transmitted to the management device 130. If the flag for QC error 1 is not set up, the sequence is shifted to step 212 and a determination is conducted whether the flag for QC error 2 is set up. If the flag for QC error 2 is set up, the sequence is shifted to step 223, in which step, a data alarm for QC error 2 is then set and the alarm is transmitted to the management device 130. If the flag for QC error 1 is not set up, an error is not occurring particularly and this status is notified to the management device 130.

Error data that has been input to the management device 130 is output to the error detection means 137 via the quality control monitoring means 1382, from which means the error data is then notified from the error detection means 137 via the error notification means 134 to the external terminals 150 of the operators corresponding to the error.

At this time, the error notification means 134 refers to the notification management table 1361 (see FIG. 4) that the storage means 135 manages, and then extracts the operators of the notification destination external terminals in accordance with monitoring result.

FIG. 4 is a conceptual diagram showing an example of displaying the notification destination management table 1361.

The notification destination management table 1361 is constructed from a control alarm "No." 301, a "Monitoring result" 302, and a "Notification operator ID" 303. The error notification means 134 identifies the operators who are logging into the system, then finds a logical product with respect to IDs listed under the "Notification operator ID" 303, and conducts notification only to operators corresponding to 'true' (i.e., of all operators registered for each kind of alarm, only those who are logging in). For example, if the data alarm for systematic error 1 exists in the monitoring result and operators 001, 002, 007, 008 are logging in, the error notification means 134 notifies, only to the operators 001, 002, error information relating to the alarm. The error notification means 134 stores the notified information into the notification result management table 1362 (see FIG. 5) that is stored within the storage means 135. In addition, in this case the external terminals 150 of the operators 001, 002 receive, through the communication means 153, the notifications from the notification means 134, and immediately after the receipt makes a pop-up display of the notified information on the display device 152.

FIG. 5 is conceptual diagram showing an example of displaying the notification result management table 1362.

The notification result management table 1362 is constructed from the following: an "Alarm management number" 401 that includes a date on which an alarm occurred, and an intra-date sequence number; an "Alarm occurrence date/time" 402 that indicates a date and time when an alarm notification instruction request was received from the error detection means 137; an "Alarm code" 403 that indicates a code for the alarm that has occurred; a "Notifier code" 404 that indicates the IDs of the notified operators; a "Troubleshooter code" 405 that indicates the IDs of the operators (troubleshooters) who have performed troubleshooting on the alarm; a "Comment" 406 that has been registered with detailed troubleshooting information by each of the troubleshooters; and a "Completion flag" 407 that indicates whether troubleshooting has been completed for the alarm.

The error notification means 134 stores the date of occurrence of the alarm and the intra-date sequence number into the "Alarm management number" 401, stores the date and time of occurrence of the alarm into the "Alarm occurrence date/time" 402, stores the alarm code into the "Alarm code" 403, and stores the notified operator ID into the "Notifier code" 404. If the troubleshooter inputs a comment, the error notification means 134 stores the comment into the "Comment" 406, and if the completion of troubleshooting is notified, the error notification means 134 sets up a relevant flag in the "Completion flag" 407.

FIG. 6 is a diagram showing an example of a screen displayed on the display means 152 of the external terminal 150.

The screen shown in FIG. 6 is displayed on the display means 152 of the external terminal 150 to indicate that an error has been notified from the management device 130. The display means 152 makes a pop-up screen display of the notified quality error information 501 including the device number, an identification code of the quality control sample, an identification code of the test item, a result of the test, an error number, and a troubleshooter identification code. The pop-up screen includes selector buttons 502 and 503 to allow the operator to select whether to troubleshoot the quality control error.

When dealing with the quality control error, the operator selects the "Yes" button 502 to troubleshoot the quality control error, or otherwise selects the "No" button 503. The buttons 502, 503 operate synchronously with the troubleshooting intention display means 155. For example, if the pop-up screen in FIG. 6 relates to the external terminal 150 of the operator 001, the selection of the "Yes" button 502 causes the troubleshooter notification means 140 of the management device 130 to store the operator ID 001 into the "Troubleshooter code" 405 of the notification result management table 1362. The troubleshooter notification means 140 also notifies to other operators that the operator 001 is the troubleshooter. The selection of the "No" button 503 causes the troubleshooter notification means 140 notifies to the other operators via the management device 130 that the operator does not have an intention to troubleshoot. Completion of such action as troubleshooting is also notified to the other operators.

FIG. 7 is a diagram showing an example of a troubleshooting result registration screen.

The processing result registration screen shown in FIG. 7 is displayed for the troubleshooter to enter details of the troubleshooting action which the troubleshooter has taken. On this screen the operator enters the quality control alarm management number 605 corresponding to the kind of error to which the troubleshooting action was taken. Quality control error number 601 is displayed upon completion of the entry. The operator then confirms the error information 601. After confirming that the error information is correct, the operator enters a necessary comment into a comment field 604 relating to a troubleshooting result of the alarm. When the troubleshooting action on the alarm is completed the operator selects a "Yes" button 602. If the troubleshooting action on the alarm is not completed, the operator selects a "No" button 603.

In the example of FIG. 7, the operator 001 deals with the QC error-1 data alarm, then enters the necessary comment into the comment field 604, and selects the "Yes" button 602 or the "No" button 603. After the management device 130 subsequently receives that information, data that denote details of troubleshooting or that say whether the troubleshooting action itself has been completed are registered in the notification result management table 1362 (see FIG. 5) of the storage means 135. Those data are also sent to other operators via the troubleshooting detail notification means 141. In this example, the operator ID 001 is registered in the "Troubleshooter code" 405 of the notification result management table 1362, and "Necessary to change probes." is registered in the "Comment" 406. In the "Completion flag" 407, '1' is registered if the "Yes" button 602 is selected on the after-troubleshooting result registration screen, or '2' is registered if the "No" button 603 is selected on that screen.

In the present embodiment, alarm information can be displayed immediately after being received, and the operator can immediately select and notify whether he or she is able to troubleshoot the alarm. The troubleshooter for the alarm can therefore be determined promptly, this information can be sent to a plurality of related operators, and thus an appropriate action can be immediately taken on the error event. In addition, information on the troubleshooter and a comment on the details of troubleshooting can be registered for the notified alarm, so that the appropriateness of the troubleshooting action can be reviewed even if the same device encounters the same or a similar error event on a later day. Furthermore, registering whether the troubleshooting action to the error has been completed enables the operator to know that some other operator has performed troubleshooting. Hence, a waste of duplicate labor relating to the processed error can be eliminated, consequently enhancing job efficiency.

Second Example

Another example of with the use of the automated analysis system according to the present embodiment is described below. The description relates to handling a lack of consumables in the analyzer 110.

Figure 8:
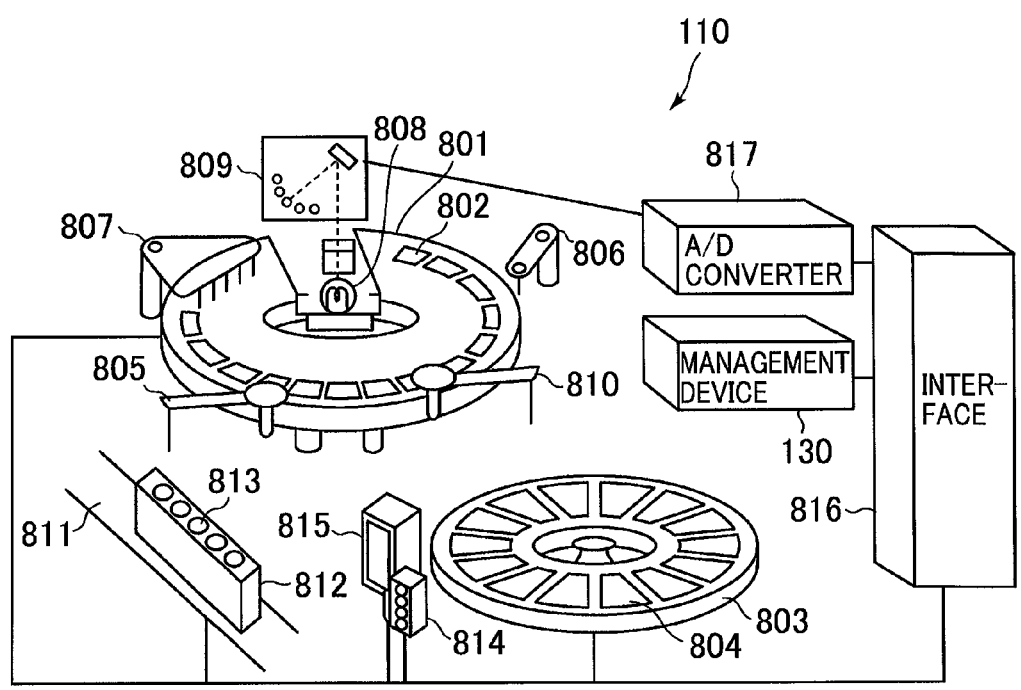
FIG. 8 is a schematic diagram showing an overall configuration of an analyzer provided in the automated analysis system according to the embodiment of the present invention.

FIG. 8 is a schematic diagram showing an overall configuration of the analyzer 110.

As shown in FIG. 8, the analyzer 110 includes: a reaction disk 801; a plurality of reaction vessels 802 set on a concentric circumference of the reaction disk 801; a reagent disk 803; a combination of reagent bottles 804 containing different kinds of reagents and set on a concentric circumference of the reagent disk 803; and a sample dispensing mechanism 805, stirrer 806, cleaning device 807, light source 808, and multi-wavelength photometer 809 arranged around the reaction disk 801, A reagent dispensing mechanism 810 is disposed between the reaction disk 801 and the reagent disk 803. In addition, a rack transport line 811 for carrying a rack is set on a rotating circumference of the sample dispensing mechanism 810, and the rack 812 moves along a surface of the rack transport line 811. A plurality of sample containers 813, each containing a sample, can be placed upright in the rack 812, and whether the sample containers 813 are placed in the rack 812 is detected with a sample container detector 814. A sample barcode, attached to each sample container 813, is read by a barcode reader 815 to identify the sample. All operation of the mechanical elements described above is controlled via an interface 816 by use of the management device 130.

The analyzer 110, while receiving instructions from the management device 130, executes the analytical operation described below.

The sample dispensing mechanism 805 dispenses a predetermined amount of sample from a sample container 813 into a reaction vessel 802. After the completion of the dispensing from the sample container 813, the rack 812 moves along the surface of the rack transport line 811 such that next sample container 813 will be positioned directly under the sample dispensing mechanism 805.

After the completion of the dispensing from all the sample containers 813 placed in the rack 812, the rack 812 is unloaded by the rack transport line 811. The reaction vessel 802 into which the sample has been dispensed above moves through rotation of the reaction disk 801. A reagent in a reagent bottle 804 is dispensed and added to the sample with the use of the reagent dispensing mechanism 810 during the movement of the reaction vessel 802. After a consequential reaction solution has been stirred by the stirrer 806, absorbance is measured with the use of the light source 808 and the multi-wavelength photometer 809. The reaction vessel 802, after the measurement, that has been used for the analysis is cleaned with the cleaning device 807.

A signal that has been obtained during the measurement of absorbance is converted through an A/D converter 817 into a digital signal which is then input to the management device 130 via the interface 816. The absorbance signal is used as a basis for measuring a substance content of the sample by use of analytical methods each set in advance for a specific kind of substance that is to be examined. The thus-measured data is compared with calibration-curve data that has been calculated from concentration data of a standard sample solution, and concentration data on the substances contained in the current sample is calculated as a result.

The reagent, contained in the reagent bottle 804, is consumed through the above processes. The reagent in the reagent bottle 804 is dispensed into the reaction vessel 802 of the reaction disk 801 by the reagent dispensing mechanism 810, and a resulting shortage of the reagent left in the bottle is notified from the consumables control means 139 (see FIG. 1) to the error detection means 137 first and then the error notification means 134, through which the same is next notified to the external terminal 150 of the relevant operator.

An initial amount of the reagent in the reagent bottle 804 is already known (e.g., equivalent to 500 tests). An alarm is therefore output from the consumables control means 139 when the amount of reagent in the bottle decreases to a threshold level (e.g., equivalent to 20 tests) predetermined on the basis of an analysis count that the consumables control means 139 controls.

In the notification destination management table 1361 shown by way of example in FIG. 4, control alarm No. 101 under the "No." 301 is a "Reagent shortage alarm" notifying that the amount of reagent in the reagent bottle has decreased below the preset threshold level, and for this alarm, the operator 001 is registered in the "Notification operator ID" 303. Additionally, control alarm No. 102 under the "No." 301 is a "Out-of-reagent alarm" notifying that the reagent in the reagent bottle has run out, and for this alarm, operators 001 to 003 are registered in the "Notification operator ID"

303. The "Out-of-reagent alarm" warns the operator about a serious status under which an unanalyzable test item could arise.

Figure 9:
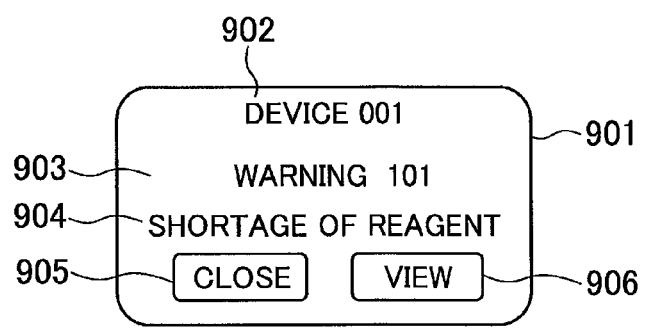
FIG. 9 is a diagram showing a display example of a notification screen notifying a lack of a residual quantity of a reagent displayed on the display means of the external terminal provided in the automated analysis system according to the embodiment of the present invention.

FIG. 9 is a diagram showing a display example of a notification screen 901 notifying a lack of a residual quantity of the reagent displayed on the display means 152 of the external terminal 150.

The notification screen 901 in FIG. 9 is presented by pop-up display on the display means 152 of the external terminal 150 upon receiving notification from the error notification means 134. The device number 902 of the analyzer 110 in which the alarm occurred, a severity level 903 of the alarm, an outline 904 of the alarm, and other data/information are displayed on the notification screen 901. Selection of a Close button 905 on the notification screen 901 exits the notification screen 901. Selection of a View button 906 displays a list of alarms.

Figure 10:
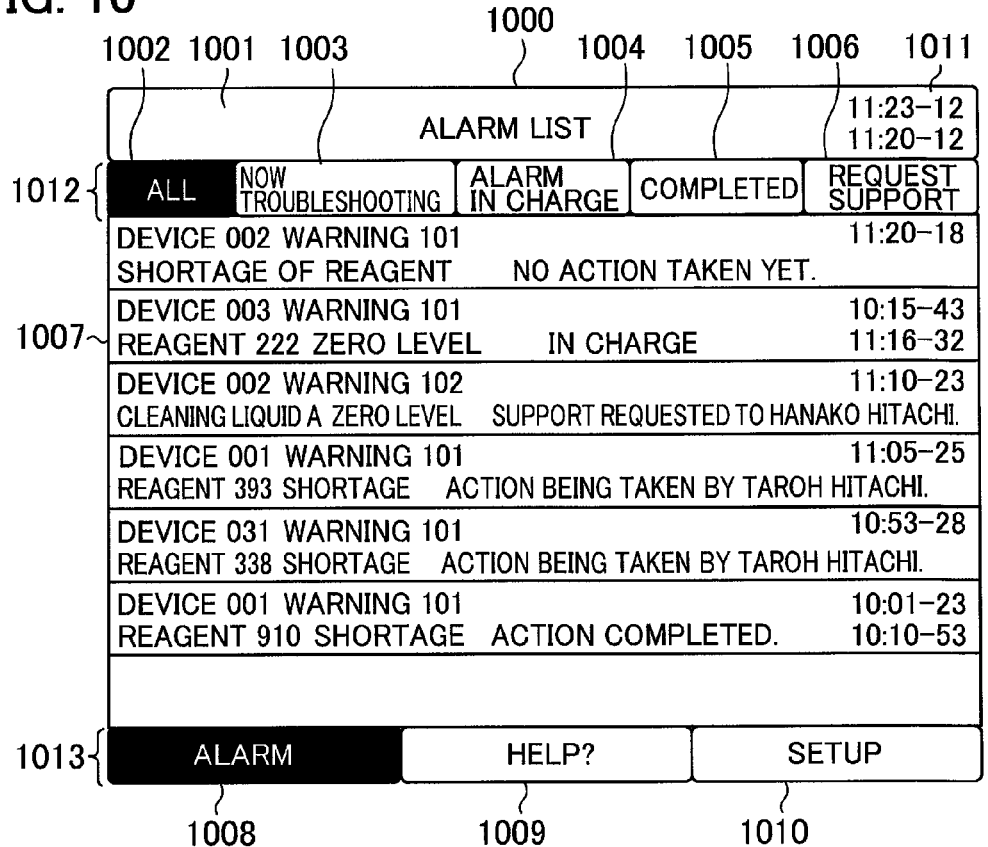
FIG. 10 is a diagram showing an example of an alarm list screen displayed at the external terminal provided in the automated analysis system according to the embodiment of the present invention.

FIG. 10 is a diagram showing an example of an alarm list screen 1001 displayed as a result of the selection of the View button 906.

The alarm list screen 1000 in FIG. 10 displays a title region 1001 that displays a title of the screen, a display parameter select button region 1012 that is used to select alarms of a type to be displayed, an alarm list screen region 1007 that lists alarms of the selected type, a display information select button region 1013 that allows various information to be displayed, and the time 1011 at which information was last acquired.

An "All" button 1002, a "Now troubleshooting" button 1003, an "Alarm in charge" button 1004, a "Completed" button 1005, and a "Request support" button 1006 are displayed in the display parameter select button region 1012.

When the "All" button 1002 is selected, all alarms currently registered in the management device 130 are displayed in the alarm list screen region 1007.

When the "Now troubleshooting" button 1003 is selected, of all alarms registered in the management device 130, only those for which troubleshooting is currently in progress and not completed are displayed in the alarm list screen region 1007.

When the "Alarm in charge" button 1004 is selected, of all alarms registered in the management device 130, only those for which the operator possessing the external terminal 150 should take charge of troubleshooting (i.e., the alarms registered for the operator if he or she has the notification operator ID 303 shown in FIG. 4), or those for which the operator took charge of troubleshooting in the past are listed in the alarm list screen region 1007.

When the "Completed" button 1005 is selected, of all alarms registered in the management device 130, only those for which troubleshooting has already been completed are displayed in the alarm list screen region 1007.

When the "Request support" button 1006 is selected, of all alarms registered in the management device 130, only those for which a support request has been sent from the troubleshooter are displayed in the alarm list screen region 1007. For example, if an alarm calling for support is occurring, the "Request support" button 1006 has its color changed to red to call attention of other operators.

Of all alarms registered in the management device 130, only those which have been selected with the use of the display parameter select buttons 1012 are displayed in time-series form in the alarm list screen region 1007, and if the list of alarms to be displayed is too large to be displayed in the screen region, this screen region can be scrolled down. The time-series display, a chronologically listed alarm representation with the latest alarm first, allows the operator to understand an occurrence status of the alarms in order with the latest alarm information first, while the alarms can instead be rearranged with the oldest one first as well. FIG. 10 shows an example in which the "All" button 1002 is selected. Names of device with its alarm having occurred, the severity levels of the alarms, an outline of the alarms, the time when the alarms occurred, and a troubleshooting status of the alarms are displayed in alarm display spaces of the alarm list screen region 1007. For example, "No action taken yet", "Action being taken", "Completed", "Support request", and "In charge" (the operator is in charge of the alarm) are displayed as the alarm troubleshooting status information. Names of the operators (as troubleshooters) in charge are displayed for the alarms that have been displayed by way of selecting the "Action being taken" button 1003 or the "Request support" button 1006. Furthermore, selection of buttons displayed at a lower section of the alarm list screen region 1007 displays further detailed information relating to each of the alarms (the display of the further detailed alarm information will be described later with the use of FIG. 11).

The display information select button region 1013 includes an "Alarm" button 1008, a "Help" button 1009, and a "Setup" button 1010. Selection of the "Alarm" button 1008 updates the alarm list screen to the latest screen information. Selection of the "Help" button 1009 displays a help screen (e.g., an instruction manual) as further detailed information on the device in which the alarm occurred. Selection of the "Setup" button 1010 displays a setting screen for selecting a form of screen display (such as screen layout) and entering an alarm notification parameter (whether receiving alarm information).

Figure 11:
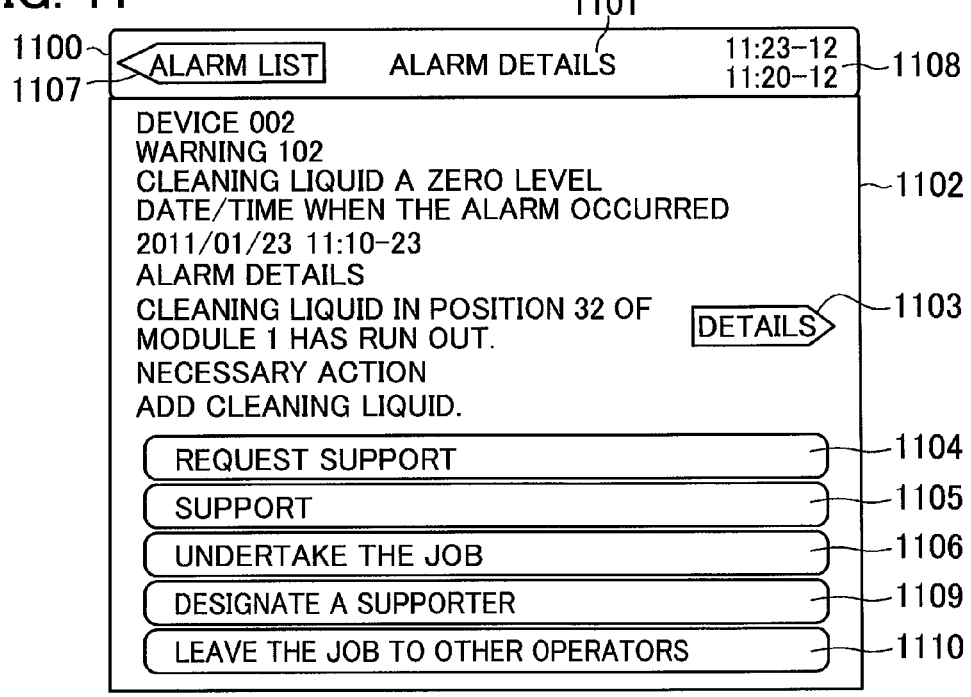
FIG. 11 is a diagram showing an example of an alarm details screen displayed at the external terminal provided in the automated analysis system according to the embodiment of the present invention.

FIG. 11 is a diagram showing an example of an alarm details screen 1100 displayed on the display means 152 when the "Alarm" button is selected in the alarm list screen region 1007.

The alarm details screen 1100 shown as an example in FIG. 11 includes: a title region 1101, an alarm detail display region 1102, a "Details" button 1103 that displays a screen corresponding to alarm details, a "Request support" button 1104 that requests support from other operators, a "Support" button 1105 that displays an intention of the operator to provide support in response to support requests from other operators, an "Undertake the job" button 1106 that displays an intention of the operator to undertake troubleshooting on the alarm, a "Designate a supporter" button 1109 that requests support from a specific operator, a "Leave the job to other operators" button 1110 that displays an intention of the operator not to be able to deal with the alarm, and an "Alarm list" button 1107 that returns control to the alarm list screen 100.

Time information 1108 that includes current time and time at which the displayed alarm information was acquired is displayed in the title region 1101. The identification number of the device in which the alarm occurred, information on where in the device the alarm occurred, the severity level of the alarm, details of the alarm, and a corrective action to be taken to the alarm are displayed in the alarm detail display region 1102. Additionally, when the "Details" button 1103 is selected, information on the reagent disk, for example, will be displayed if the alarm relates to a quantitative shortage of the reagent (this alarm will be described later with FIG. 12).

When the "Request support" button 1104 is selected, a notification of a support request is sent from the support request intention display means 156. Upon receiving the notification, the management device 130 conducts a support request notification via the support request notification means 142 to the other operators who are registered in the "Notification operator ID" 303 of the notification destination management table 1361. A pop-up display of the support request notification appears at the external terminals 150 of those registered operators.

When the "Support" button 1105 is selected, a notification of the operator's intention to provide support is sent from the support intention display means 157. Upon receiving the notification, the management device 130 additionally registers the identification code of this operator who has showed his/her intention to provide the support, under the "Troubleshooter code" 405 of the notification result management table 1362. The management device 130 also notifies the operator as a supporter via the supporter notification means 143 to the other operators who are registered for this alarm in the notification destination management table 1361.

When the "Undertake the job" button 1106 is selected, a notification of the operator's intention to undertake troubleshooting is sent from the troubleshooting intention display means 155. Upon receiving the notification, the management device 130 registers the identification code of this operator who has showed his/her intention to undertake troubleshooting under the "Troubleshooter code" 405 of the notification result management table 1362. The management device 130 also notifies the operator as a supporter via the troubleshooter notification means 140 to the other operators who are registered for this alarm in the notification destination management table 1361.

When the "Designate a supporter" button 1109 is selected, a notification designating a support operator is sent from the designated person notification means 154. Upon receiving the notification, the management device 130 notifies to the designated operator that he or she has been designated as a supporter, via the designated person contact means 145. In addition, a pop-up display of the supporter designating notification appears at the external terminal 150 of the designated operator.

When the "Leave the job to other operators" button 1110 is selected, a notification indicating that the operator is not able to provide the support is sent from the non-support intention display means 158. Upon receiving the notification, the management device 130 notifies, via the non-supporter notification means 144, to the other operators who are registered for this alarm in the notification destination management table 1361 that the particular operator is not able to provide the support.

Figure 12:
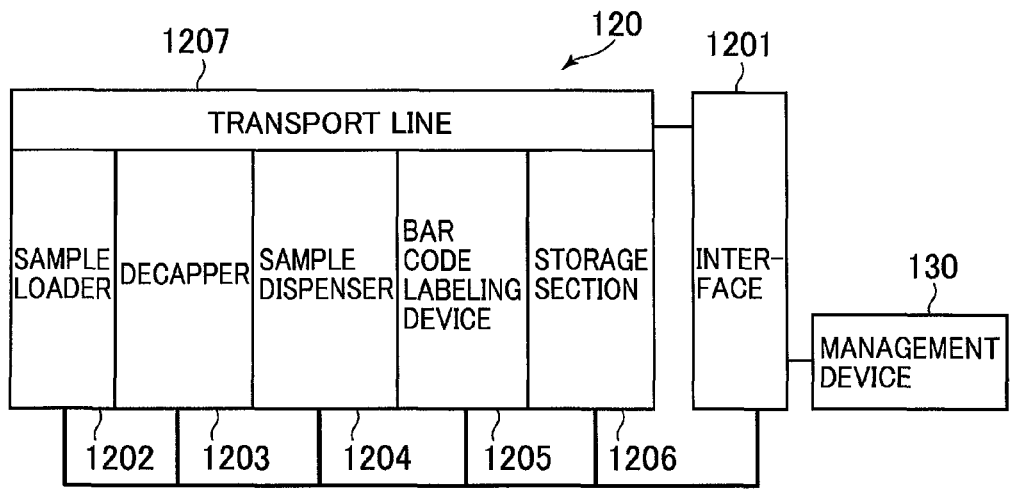
FIG. 12 is a schematic diagram showing an overall structure of a processing device provided in the automated analysis system according to the embodiment of the present invention.

FIG. 12 is a diagram showing an example of a reagent usage status displayed on the display means 152 when the "Details" button 1103 is selected in the "Alarm details" display screen region 1101.

Figure 13:
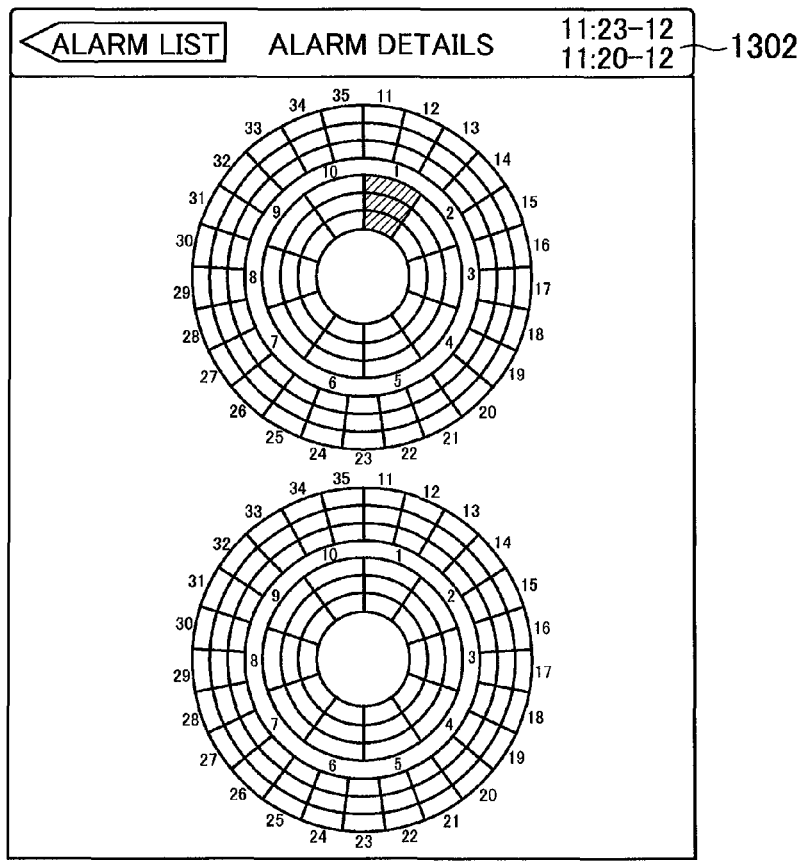
FIG. 13 is a diagram showing an example of a reagent usage status displayed on the display means of the external terminal provided in the automated analysis system according to the embodiment of the present invention.

A section in which the reagent in a reagent bottle is running short is marked with hatching on a reagent disk alarm details screen 1302 shown in FIG. 13. During an actual operation, the amount of reagent left in the reagent bottle is appropriately displayed in color-coded form in accordance with a particular usage status of the reagent. For example, a section with out of reagent is displayed in red, a section with the quantitative shortage of the reagent (below the threshold level) is displayed in yellow, a section with a sufficient amount of reagent is displayed in blue, and a section without a reagent is displayed in white (blanc). The color-coded display enables the operator to visually confirm the amount of reagent left in the bottle. In a reagent disk model diagram, which is displayed on the alarm details screen 1302, positions (addresses) on the reagent disk are shown so that the operator can readily recognize a section at which to take a necessary action. Thus the reagent can be replaced efficiently.

In the present example, since the information relating to the amount of reagent left in the reagent bottle 804 can be referred to with the use of the external terminal 150, the operator can readily recognize a more specific position at which the reagent bottle is to be replaced, and efficiently replace the reagent as well. In addition, the operator can confirm only alarms, which he or she takes charge of, among all those which have been notified to the operator. This feature leads to preventing an alarm-troubleshooting omission from occurring. Furthermore, since the operator can confirm an alarm for which the support has been requested, he or she can confirm presence/absence of an alarm for which there is a delay in troubleshooting, and act dynamically and flexibly in accordance with a particular progress of troubleshooting. These features and characteristics of the present example contribute to speedy resolution of the error event. Moreover, the operator can confirm an occurrence status of all alarms in the system since the operator can list all notified alarms in addition to the alarms that he/she takes charge of or for which the support for troubleshooting has been requested.

Third Example

Yet another example of with the use of the automated analysis system according to the present embodiment is described below. The description relates to handling a lack of consumables in the processing device used for sample pre-processing.

FIG. 12 is a schematic diagram showing an overall structure of the processing device 120.

As shown in FIG. 12, the processing device 120 includes a sample container loader 1202, a decapper 1203 that opens a cap of a sample container containing a sample, a sample dispenser 1204 that dispenses the sample from the decapped sample container into a second container, a bar code labeling device 1205 that attaches a barcode to the second container into which the sample has been dispensed from the decapped sample container, a storage unit 1206 for storing the sample container and the container to which the barcode has been attached, a transport line 1207 that connects the above-described elements of the processing device 120 and transports the sample container and the second container having the barcode attached thereto, and an interface 1201 for controlling all elements of the processing device 120. The interface is connected to the management device 130.

A sample container that has been provided in the sample loader 1202 moves along the surface of the transport line 1207 and is transported to the decapper 1203. The decapper 1203 performs the process of opening the cap of the sample container. The sample container whose cap has been opened moves along the surface of the transport line 1207 and is transported to the sample dispenser 1204. The sample dispenser 1204 dispenses the sample from the sample container into a second container with the use of a throw-away sampling tube in order to prevent sample-to-sample contamination. The sample container with the dispensed sample moves along the surface of the transport line 1207 and is transported to and stored into the storage unit 1206. The second container with the dispensed sample moves along the surface of the transport line 1207 and is transported to the bar code labeling device 1205. The bar code labeling device 1205 attaches a barcode to the second container. The bar-coded second container moves along the surface of the transport line 1207 and is transported to and stored into the storage unit 1206. All the operation of these elements is controlled by the management device 130 via the interface 1201.

Figure 14:
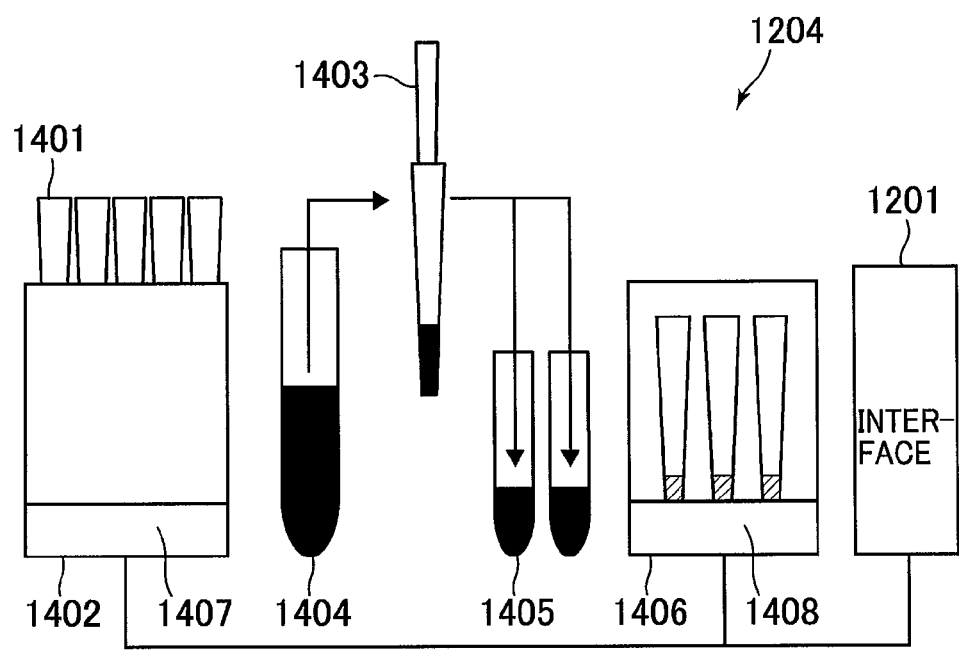
FIG. 14 is a schematic diagram showing a structure of a sample dispenser constituting the processing device provided in the automated analysis system according to the embodiment of the present invention.

FIG. 14 shows a configuration of the sample dispenser 1204. The sample dispenser 1204 includes a tube setter 1402 that sets a throw-away sampling tube, a discarder 1406 that discards a used sampling tube, and a dispensing mechanism 1403 that dispenses a sample. The tube setter 1402 and the discarder 1406 are connected to the interface 1201.

Upon completion of transport of a sample container 1404 to the sample dispenser 1204, the dispensing mechanism 1403 removes a sampling tube 1401 from the tube setter 1402 and then mounts the sampling tube 1401 properly in the dispensing mechanism 1403. The dispensing mechanism 1403 uses the sampling tube 1401 to aspirate a necessary amount of sample from the sample container 1404, then carry this sample to a second container 1406 into which the sample is discharged. After these actions, the dispensing mechanism 1403 sends the sampling tube 1403 to the discarder 1406 where the sampling tube 1403 is then discarded. All the operation of these elements is controlled by the management device 130 via the interface 1201.

The sampling tube 1401, placed in the tube setter 1402, is consumed through the above processes. The sampling tube 1401 in the tube setter 1402 is put into sample-dispensing use by the dispensing mechanism 1403, and then discarded by the discarder 1406. A resulting shortage of sampling tubes left in the tube setter 1402 is notified from the consumables control means 139 (see FIG. 1) to the error detection means 137 first and then the error notification means 134, through which the same is next notified to the external terminal 150 of the relevant operator.

The quantity of sampling tubes 1401 left in the tube setter 1402 is handled as follows: an alarm is output from the consumables control means 139 when a residual tube quantity sensor 1407 in the tube setter 1402 senses that the quantity of sampling tubes 1401 in the tube setter 1402, controlled by the consumables control means 139, decreases to a preset threshold level (e.g., equivalent to 50 samples).

In the notification destination management table 1361 shown by way of the example in FIG. 4, control alarm No. 1401 under the "No." 301 is a "Tube shortage alarm" notifying that the quantity of sampling tubes in the tube setter has decreased below the preset threshold level, and for this alarm, operator 401 is registered in the "Notification operator ID" 303. Additionally, control alarm No. 1402 under the "No." 301 is a "Out-of-tube alarm" notifying that the quantity of sampling tubes in the tube setter has run out, and for this alarm, operators 401, 402 are registered in the "Notification operator ID" 303. The "Out-of-tube alarm" warns the operator about a serious status that the tube shortage could lead to sample dispensing not being continuable.

Figure 15:
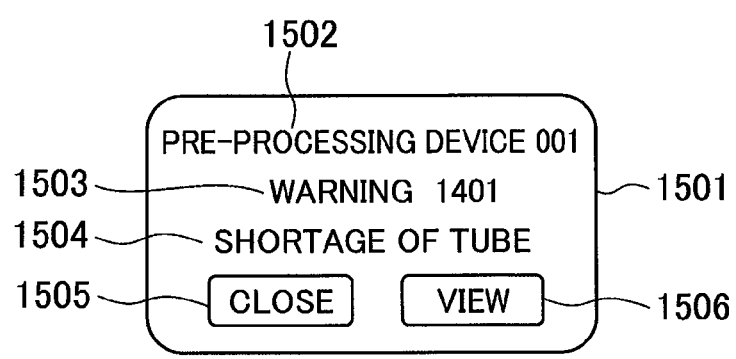
FIG. 15 is a diagram showing a display example of a notification screen notifying a lack of a residual quantity of tubes and displayed on the display means of the external terminal provided in the automated analysis system according to the embodiment of the present invention.

FIG. 15 is a diagram showing a display example of a notification screen 1501 notifying a lack of a residual quantity of tubes, displayed on the display means 152 of the external terminal 150.

The notification screen 1501 in FIG. 15 is presented by pop-up display on the display means 152 of the external terminal 150 upon receiving notification from the error notification means 134. The device number 1502 of the processing device 120 in which the alarm occurred, a severity level 1503 of the alarm, an outline 1504 of the alarm, and other data/information are displayed on the notification screen 1501. Selection of a Close button 1505 on the notification screen 1501 exits the notification screen 1501. Selection of a View button 1506 displays a list of alarms.

FIG. 16 is a diagram showing an example of an analyzer/processing device alarm list screen 1601 displayed as a result of the selection of the View button 1506. On this screen, all analyzer and processing device alarms can be viewed in one screen region.

Upon receiving this alarm notification, the operator sets a sampling tube 1401 in the tube setter 1402 of the sample dispenser in accordance with contents of the alarm. The sampling tube setter 1402 recognizes via the residual tube quantity sensor 1407 that the sampling tube 1401 has been set. The residual quantity of sampling tubes that has thus been updated is notified from the consumables control means 139 to the error detection means 137. Additionally, control alarm No. 11401 or 11402 under the "No." 301 is notified to the external terminal 150 of relevant operators. This makes it unnecessary for the operators to execute the error troubleshooting completion notification from the processing result registration screen shown in FIG. 7.

In the present example, since the information relating to the residual quantity of sampling tubes 1401 can be viewed with the use of the external terminal 150, a more specific corrective action to be followed can be readily understood and the action can be taken promptly. In addition, the occurrence status of alarms in the entire analysis system and the progress of troubleshooting can be confirmed since all notified alarms relating to the analyzer as well as the processing device can be listed.

Furthermore, the result of troubleshooting by the operator is sensor-detected, which makes error troubleshooting completion notification unnecessary, thus further reducing a burden upon the operator.

REFERENCE NUMERALS

100 Automated analysis system
110 Analyzer
120 Processing device
130 Management device
133 Registration means
134 Error notification means
135 Storage means
136 Operator notification management table
137 Error detection means
140 Troubleshooter notification means
141 Troubleshooting detail notification means
142 Support request notification means
143 Supporter notification means
150 External terminal
155 Troubleshooting intention display means
156 Support request intention display means
157 Support intention display means
158 Non-support intention display means
1000 Alarm list screen

The invention claimed is:
1. An automated analysis system comprising:
at least one of an analyzer that analyzes a sample and a processing device that pre-processes the sample;
a management device that manages the at least one of the analyzer and the processing device, and
a plurality of display devices connected to the management device,
wherein the management device includes:

means that detects a plurality of different kinds of errors in the at least one of the analyzer and the processing device;

storage means having stored therein an operator notification management table in which a plurality operators are registered to handle each of the different kinds of the errors; and means that notifies at least two operators that are to handle each of the respective errors detected by the error detection means based on the operator notification management table and the kind of the respective errors, wherein each of the display devices includes:

means that selects one of a plurality of alarms from an alarm list screen displayed on the respective display device, where each of the alarms corresponds to one of the errors detected by the error notification means and each of the alarms includes identification of the at least one of the analyzer and the processing device in which the respective error has occurred, a severity level of the respective error, an outline of the respective error, a time when the respective error occurred, and a troubleshooting status of the respective error, and where the alarm list screen is displayed on the display devices when a notification of the at least two operators that are to handle one of the errors is received; and means that registers one of the at least two operators, who is handling the respective error corresponding to the selected one of the alarms, as a troubleshooter from among the at least two operators, where the registering of the one of the at least two operators as the troubleshooter is based on an operation of an alarm details screen that displays detailed information of the respective error corresponding to the selected one of the alarms, the alarm details screen being displayed when the one of the at least two operators that received the notification selects the one of the alarms from the alarm list screen, wherein the management device further includes:

means to notify a support request of the troubleshooter to the at least two operators other than the troubleshooter; and supporter notification means to notify identification information on another one of the at least two operators who is not able to accept the support request to the at least two operators other than the other one of the at least two operators that have the intention of not being able to accept the support request, and wherein each of the display devices corresponding to the at least two operators further include:

troubleshooting intention display means to display an intention of the at least two operators to troubleshoot the respective error corresponding to the selected one of the alarms; and non-support intention display means to display an intention of the at least two operators not to provide support in response to the support request from the troubleshooter.

2. The automated analysis system according to claim 1, wherein the management device includes:

troubleshooter notification means that notifies identification information on the troubleshooter to the at least two operators other than the troubleshooter.

3. The automated analysis system according to claim 1, wherein each of the display devices includes:

means that notifies a detail of troubleshooting by the troubleshooter to the at least two operators other than the troubleshooter.

4. The automated analysis system according to claim 1, wherein the management device includes:

supporter notification means that notifies identification information on another one of the at least two operators who has accepted the support request to the at least two operators other than the other one of the at least two operators who has accepted the support request.

5. The automated analysis system according to claim 1, wherein:

at least one of the errors is a quality control error or a shortage of consumable error.

6. An automated analysis system comprising:

at least one of an analyzer that analyzes a sample and a processing device that pre-processes the sample;

a management device that manages the at least one of the analyzer and the processing device; and a plurality of hand-held terminals that each have a display device and that correspond to a plurality of operators that respectively carry the terminals, wherein the management device includes:

means that detects a plurality of different kinds of errors in the at least one of the analyzer and the processing device;

storage means having stored therein an operator notification management table in which the plurality of operators are registered to handle each of the different kinds of the errors; and means that notifies at least two of the terminals corresponding to at least two operators that are to handle each of the respective errors detected by the error detection means based on the operator notification management table and the kind of the respective errors, wherein each of the terminals includes:

means that selects one of a plurality of alarms from an alarm list screen displayed on the respective terminal, where each of the alarms corresponds to one of the errors detected by the error notification means and each of the alarms includes identification of the at least one of the analyzer and the processing device in which the respective error has occurred, a severity level of the respective error, an outline of the respective error, a time when the respective error occurred, and a troubleshooting status of the respective error, and where the alarm list screen is displayed on the at least two of the terminals when a notification of the at least two operators that are to handle one of the errors is received; and means that registers one of the at least two operators, who is handling the respective error corresponding to the selected one of the alarms, as a troubleshooter from among the at least two operators, where the registering the one of the at least two operators as the troubleshooter is based on an operation of an alarm details screen that displays detailed information of the respective error corresponding to the selected one of the alarms, the alarm details screen being displayed on each display device of the terminals corresponding to the at least two operators when the terminals corresponding to the at least two operators receive the notification to handle the respective error corresponding to the selected one of the alarms, wherein the management device further includes:

means to notify a support request of the troubleshooter to the at least two operators other than the troubleshooter; and supporter notification means to notify identification information on another one of the at least two operators who is not able to accept the support request to the at least two operators other than the other one of the at least two operators that have the intention of not being able to accept the support request, and wherein each of the terminals corresponding to the at least two operators further include:

troubleshooting intention display means to display an intention of the at least two operators to troubleshoot the respective error corresponding to the selected one of the alarms; and non-support intention display means to display an intention of the at least two operators not to provide support in response to the support request from the troubleshooter.

7. The automated analysis system according to claim 6, wherein:

each of the terminals corresponding to the at least two operators includes troubleshooting intention display means to display an intention of the respective operator to troubleshoot the respective error corresponding to the selected one of the alarms; and the management device includes troubleshooter notification means to notify identification information on the troubleshooter to the at least two operators other than the troubleshooter.

8. The automated analysis system according to claim 6, wherein:

each of the terminals corresponding to the at least two operators includes means to display an intention of the least two operators to provide support in response to the support request from the troubleshooter; and the management device includes supporter notification means to notify identification information on another one of the at least two operators who has accepted the support request to the at least two operators other than the other one of the at least two operators who has accepted the support request.

9. The automated analysis system according to claim 6, wherein each of the terminals corresponding to the at least two operators includes means to request support to a specific one of the at least two operators other than the troubleshooter via the management device as the support request.

10. The automated analysis system according to claim 6, wherein:

each of the terminals corresponding to the at least two operators has a visual data acquisition function and an audio recording function; and the management device includes means to notify visual data or audio data recorded in the terminal to the at least two operators other than the troubleshooter or an upper-level administrator.

11. The automated analysis system according to claim 6, wherein each of the terminals corresponding to the at least two operators includes means to visually display location information of a reagent placed in a reagent disk corresponding to the respective error.

12. The automated analysis system according to claim 6, wherein the terminal of the troubleshooter displays an instruction manual of the at least one of the analyzer and the processing device in which the respective error has occurred.

* * * * *